(12) United States Patent
Riley et al.

(10) Patent No.: US 6,582,590 B1
(45) Date of Patent: *Jun. 24, 2003

(54) MULTISTAGE HYDROPROCESSING USING BULK MULTIMETALLIC CATALYST

(75) Inventors: Kenneth Lloyd Riley, Baton Rouge, LA (US); Darryl Patrick Klein, Ellicott City, MD (US); Zhiguo Hou, Baton Rouge, LA (US); Stuart Leon Soled, Pittstown, NJ (US); Michael Charles Kerby, Baton Rouge, LA (US); Gary Brice McVicker, Califon, NJ (US); Edward Stanley Ellis, Fairfax, VA (US); Michele Sue Touvelle, Baton Rouge, LA (US); Sabato Miseo, Pittstown, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/869,982

(22) PCT Filed: Jan. 14, 2000

(86) PCT No.: PCT/US00/00979

§ 371 (c)(1),
(2), (4) Date: Aug. 22, 2001

(87) PCT Pub. No.: WO00/42124

PCT Pub. Date: Jul. 20, 2000

Related U.S. Application Data

(63) Continuation-in-part of application No. 09/231,156, filed on Jan. 15, 1999, now Pat. No. 6,162,350, which is a continuation-in-part of application No. 08/900,389, filed on Jul. 15, 1997, now Pat. No. 6,156,695.

(51) Int. Cl.[7] .......... C10G 45/00; C10G 45/04; C10G 45/60
(52) U.S. Cl. .......... 208/210; 208/213; 208/216 R; 208/217; 208/254 R; 208/254 H
(58) Field of Search .......... 208/210, 213, 208/216 R, 217, 254 R, 254 H

(56) References Cited

U.S. PATENT DOCUMENTS

| | | | |
|---|---|---|---|
| 4,596,785 A | 6/1986 | Toulhoat et al. | 502/220 |
| 4,875,992 A | 10/1989 | Hamner | 208/89 |
| 5,292,428 A | * 3/1994 | Harrison et al. | 208/208 R |
| 5,968,346 A | 10/1999 | Jung et al. | 208/210 |
| 6,162,350 A | * 12/2000 | Soled et al. | 208/113 |

FOREIGN PATENT DOCUMENTS

| | | | |
|---|---|---|---|
| EP | 0277718 | 10/1988 | C10G/65/08 |
| WO | WO 99/03578 | 1/1999 | B01J/23/883 |

* cited by examiner

Primary Examiner—Walter D. Griffin
Assistant Examiner—Tam M. Nguyen
(74) Attorney, Agent, or Firm—Paul E. Purwin; George B. Georgellis

(57) ABSTRACT

Sulfur content of distillate feedstock, which is greater than 3,000 wppm, is reduced using multi-stage hydrodesulfurization by reacting the feestream in stages with reaction zone(s) containing bulk multimetallic catalyst comprised of Group VIII non-noble metal(s) and at least two group VIB metals. The ratio of Group VIB to Group VIII non-noble metals is 10:1 to 1:10.

26 Claims, 2 Drawing Sheets

MULTISTAGE HYDROPROCESSING USING BULK MULTIMETALLIC CATALYST

CROSS REFERENCE TO RELATED APPLICATIONS

This is a continuation-in-part of U.S. Ser. No. 09/231,156 filed on Jan. 15, 1999, now U.S. Pat. No. 6,162,350 which is a continuation-in-part of U.S. Ser. No. 08/900,389, which was filed on Jul. 15, 1997, now U.S. Pat. No. 6,156,695.

FIELD OF THE INVENTION

This invention relates to a multistage hydrodesulfurizing process for producing low sulfur distillates. A distillate boiling range feedstock containing in excess of about 3,000 wppm sulfur is hydrodesulfurized in a first hydrodesulfurizing stage containing one or more reaction zones in the presence of hydrogen and a hydrodesulfurizing catalyst. The liquid product stream thereof is passed to a first separation stage wherein a vapor phase product stream and a liquid product stream are produced. The liquid product stream, which has a substantially lower sulfur and nitrogen content then the original feedstream is passed to a second hydrodesulfurizing stage also containing one or more reaction zones where it is reacted in the presence of hydrogen and a second hydrodesulfurizing catalyst at hydrodesulfurizing conditions. The liquid product stream from this second hydrodesulfurizing stage is passed to a third reaction stage containing one or more reaction zones wherein said liquid product stream is hydrogenated in presence of a third catalyst in the presence of hydrogen and at hydrogenation conditions. The catalyst in any one or more reaction zones is a bulk multimetallic catalyst comprised of at least one Group VIII non-noble metal and at least two Group VIB metals wherein the ratio Group VIB metals to Group VIII non-noble metal is from about 10:1 to about 1:10.

BACKGROUND OF THE INVENTION

Environmental and regulatory initiatives are requiring ever lower levels of both sulfur and aromatics in distillate fuels. For example, proposed sulfur limits for distillate fuels to be marketed in the European Union for the year 2005 is 50 wppm or less. There are also regulations that will require lower levels of total aromatics in hydrocarbons and, more specifically, to lower levels of multiring aromatics found in distillate fuels and heavier hydrocarbon products. Further, the maximum allowable aromatics level for U.S. proposed diesel, CARB reference diesel, and Swedish Class I diesel are 35, 10 and 5 vol. %, respectively. Further, the CARB and Swedish Class I diesel fuels allow no more than 1.4 and 0.02 vol. % polyaromatics, respectively. Consequently, much work is presently being done in the hydrotreating art because of these proposed regulations.

Hydrotreating, or in the case of sulfur removal, hydrodesulfurization, is well known in the art and typically requires treating the petroleum streams with hydrogen in the presence of a supported catalyst at hydrotreating conditions. The catalyst is usually comprised of a Group VI metal with one or more Group VIII metals as promoters on a refractory support. Hydrotreating catalysts that are particularly suitable for hydrodesulfurization, as well as hydrodenitrogenation, generally contain molybdenum or tungsten on alumina promoted with a metal such as cobalt, nickel, iron, or a combination thereof Cobalt promoted molybdenum on alumina catalysts are most widely used when the limiting specifications are hydrodesulfurization, while nickel promoted molybdenum on alumina catalysts are the most widely used for hydrodenitrogenation, partial aromatic saturation, as well as hydrodesulfurization.

Much work is also being done to develop more active catalysts and improved reaction vessel designs in order to meet the demand for more effective hydroprocessing processes. Various improved hardware configurations have been suggested. One such configuration is a countercurrent design wherein the feedstock flows downwardly through successive catalyst beds counter to upflowing treat gas, which is typically a hydrogen containing treat-gas. The downstream catalyst beds, relative to the flow of feed, can contain high performance, but otherwise more sulfur sensitive catalysts because the upflowing treat gas carries away heteroatom components, such as $H_2S$ and $NH_3$, that are deleterious to sulfur and nitrogen sensitive catalysts.

A family of compounds related to hydrotalcites, e.g., ammonium nickel molybdate, has been prepared as an approach to improved hydrotreating catalysts. Whereas X-ray diffraction analysis has shown that hydrotalcites are composed of layered phases with positively charged sheets and exchangeable anions located in the galleries between the sheets, the related ammonium nickel molybdate phase has molybdate anions in interlayer galleries bonded to nickel oxyhydroxide sheets. See, for example, Levin, D., Soled, S. L., and Ying, J. Y., Crystal Structure of an Ammonium Nickel Molybdate prepared by Chemical Precipitation, Inorganic Chemistry, Vol. 35, No. 14, p. 4191–4197 (1996). The preparation of such materials also has been reported by Teichner and Astier, Appl. Catal. 72, 321–29 (1991); Ann. Chim. Fr. 12, 337–43 (1987), and C. R. Acad. Sci. 304 (II), #11, 563–6 (1987) and Mazzocchia, Solid State Ionics, 63–65 (1993) 731–35.

Now, when molybdenum is partially substituted for by tungsten, an amorphous phase is produced which upon decomposition and, preferably, sulfidation, provides enhanced hydrodenitrogenation (HDN) catalyst activity relative to the unsubstituted (Ni—Mo) phase.

SUMMARY OF THE INVENTION

In accordance with this invention there is provided a multistage hydroprocessing process comprising:

a) reacting a feedstream in a first hydroprocessing stage in the presence of a hydrogen-containing treat gas, the first hydroprocessing stage containing one or more reaction zones, each reaction zone operated at first stage hydroprocessing conditions and in the presence of a hydroprocessing catalyst, thereby resulting in a first liquid product stream;

b) passing the first liquid product stream to a first separation zone where a first vapor phase product stream and a first liquid phase product stream are produced;

c) reacting the first liquid phase product stream of b) in a second hydroprocessing stage in the presence of a hydrogen-containing treat gas, the second hydroprocessing stage containing one or more second stage reaction zones operated at second stage hydroprocessing conditions wherein each or reaction zone contains a bed of hydrotreating catalyst, thereby resulting in a second liquid product stream;

d) passing the second liquid product stream of step c) to a second separation zone wherein a second vapor phase stream and a second liquid phase stream are produced;

e) reacting the second liquid phase stream from d) in a third reaction stage in the presence of a hydrogen-containing treat gas, the third hydroprocessing stage containing one or more reaction zones operated at third stage hydroprocessing conditions in the presence of a third hydrotreating catalyst, in order to form a third liquid product stream;

f) passing the third liquid product stream to a third separation zone wherein a third vapor phase stream and a third liquid phase stream are produced; and g) collecting both the third vapor phase stream and the third liquid phase stream; and wherein at least one of the reaction zones of at least on of said hydrodesulfurizing stages contains a bulk multimetallic catalyst comprised of at least one Group VIII non-noble metal and at least two Group VIB metals and wherein the ratio of Group VIB metal to Group VII non-noble metal is from about 10:1 to about 1:10.

In a preferred embodiment of the present invention the Group VIII non-noble metal is selected from Ni and Co and the Group VIB metals are selected from Mo and W.

In another preferred embodiment of the present invention two Group VIB metals are present as Mo and W and the ratio of Mo to W is about 9:1 to about 1:9.

In yet another preferred embodiment of the present invention the bulk multimetallic is represented by the formula:

$$(X)_b(Mo)_c(W)_d O_z$$

wherein X is one or more Group VIII non-noble metal, and the molar ratio of b:(c+d) is 0.5/1 to 3/1, preferably 0.75/1 to 1.5/1, more preferably 0.75/1 to 1.25/1.

In still another preferred embodiment of the present invention the molar ratio of c:d is preferably >0.01/1, more preferably >0.1/1, still more preferably 1/10 to 10/1, still more preferably 1/3 to 3/1, most preferably substantially equimolar amounts of Mo and W, e.g., 2/3 to 3/2; and z=[2b+6(c+d)]/2.

In another preferred embodiment of the present invention the essentially amorphous material has a unique X-ray diffraction pattern showing crystalline peaks at d=2.53 Angstroms and d=1.70 Angstroms.

In still another preferred embodiment of the present invention the Group VIII non-noble metal is nickel.

In still another preferred embodiment of the present invention at least a portion of the vapor product stream from the first separation zone is recycled to the first hydrodesulfurization stage.

In another preferred embodiment of the present invention at least a portion of the vapor product stream from the second separation stage is cascaded to said first hydrodesulfurization stage.

DETAILED DESCRIPTION OF THE INVENTION

Figure 1:
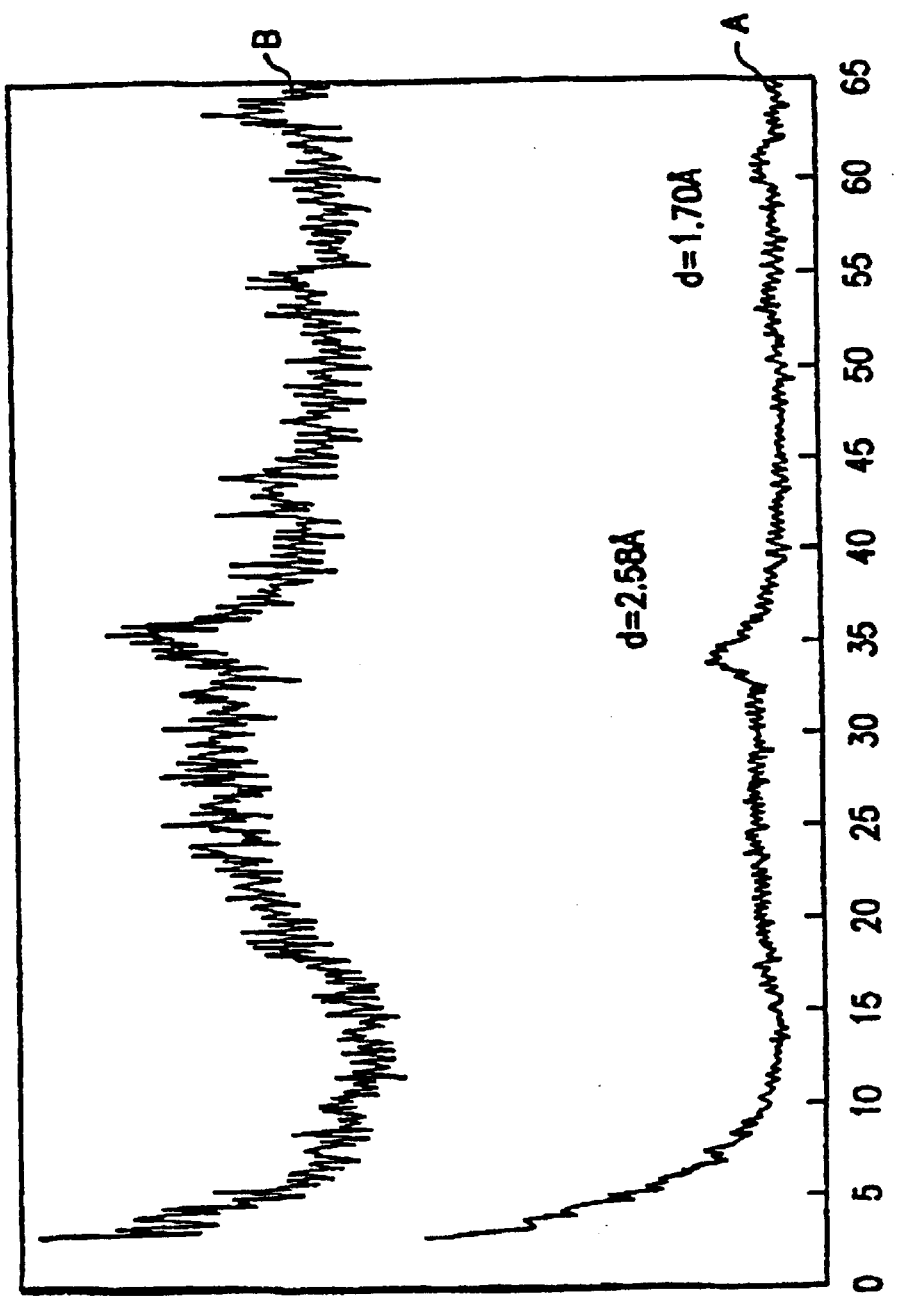
FIG. 1 is the X-ray diffraction pattern of a Ni—Mo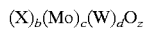$_{0.5}$W$_{0.5}$—O compound prepared by boiling precipitation before calcining (Curve A) and after calcining 400° C. (Curve B). Note that the patterns for both the precursor and the decomposition product of the precursor are quite similar with the two peaks at essentially the same place. The ordinate is relative intensity; the abscissa is two theta (degrees).
Figure 2:
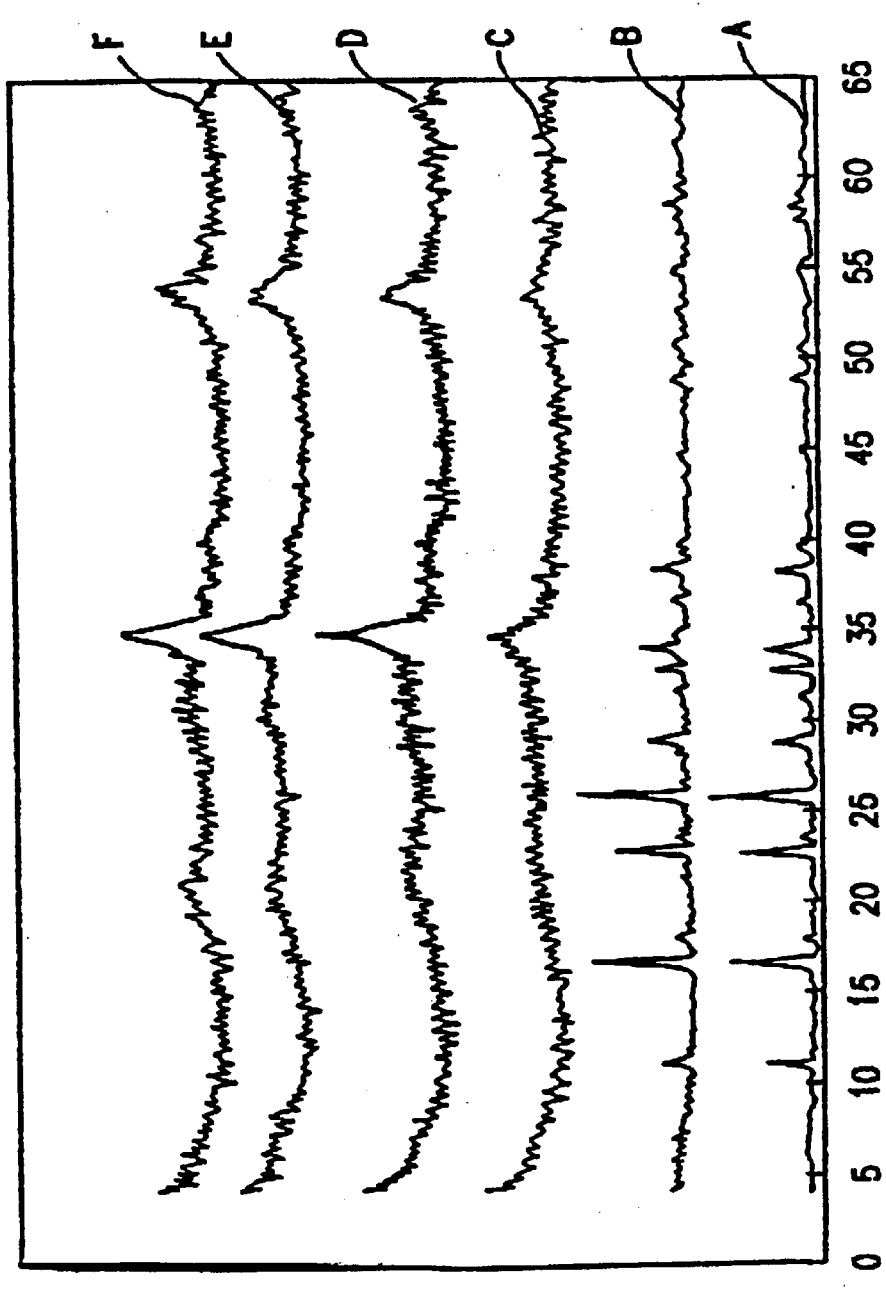
FIG. 2 shows the X-ray diffraction patterns, by CuKα radiation (λ=1.5405 Å), of Ni—Mo$_{1-x}$—W$_x$—O precursors wherein curve A is Mo$_{0.9}$W$_{0.1}$, curve B is Mo$_{0.7}$W$_{0.3}$, curve C is Mo$_{0.5}$W$_{0.5}$, curve D is Mo$_{0.3}$W$_{0.7}$, curve E is Mo$_{0.1}$W$_{0.9}$, and curve F is Mo$_O$W$_1$. The ordinate and abscissa are as described for FIG. 1.

The invention is based in part on the discovery that molybdenum in a nickel-molybdenum oxide phase may be partially substituted by tungsten. The resulting phase is an essentially ammonia-free, substantially amorphous oxide which upon sulfidation provides enhanced hydroprocessing activity relative to the unsubstituted Ni—Mo phase. The invention is also based in part on the discovery of catalysts containing at least one Group VIII non-noble metal and at least two Group VIB metals, wherein the ratio of Group VIB metal to Group VIII non-noble metal ranges from about 10:1 to about 1:10.

The bulk multimetallic catalyst composition used in the practice of the present invention can be used in virtually all hydroprocessing processes to treat a plurality of feeds under wide-ranging reaction conditions such as temperatures of from 200 to 450° C., hydrogen pressures of from 5 to 300 bar, liquid hourly space velocities of from 0.05 to 10 h$^{-1}$ and hydrogen treat gas rates of from 35.6 to 1780 m$^3$/m$^3$ (200 to 10000 SCF/B). The term "hydroprocessing" encompasses all processes in which a hydrocarbon feed is reacted with hydrogen at the temperatures and pressures noted above, and include hydrodemetallation, hydrodewaxing, hydrotreating, hydrogenation, hydrodesulfurization, hydrodenitrogenation, hydrodearomatization, hydroisomerization, and hydrocracking including selective hydrocracking. Depending on the type of hydroprocessing and the reaction conditions, the products of hydroprocessing may show improved viscosities, viscosity indices, saturates content, low temperature properties, volatilities and depolarization. It is to be understood that hydroprocessing of the present invention can be practiced in one or more reaction zones and can be practiced in either countercurrent flow or cocurrent flow mode. By countercurrent flow mode we mean a process mode wherein the feedstream flows countercurrent to the flow of hydrogen-containing treat gas. The hydroprocessing reactor can also be operated in any suitable catalyst-bed arrangement mode. For example, it can be a fixed bed, slurry bed, or ebulating bed.

A wide range of petroleum and chemical feedstocks can be hydroprocessed in accordance with the present invention. Suitable feedstocks include whole and reduced petroleum crudes, atmospheric and vacuum residua, propane deasphalted residua, e.g., brightstock, cycle oils, FCC tower bottoms, gas oils, including atmospheric and vacuum gas oils and coker gas oils, light to heavy distillates including raw virgin distillates, hydrocrackates, hydrotreated oils, dewaxed oils, slack waxes, Fischer-Tropsch waxes, raffinates, naphthas, and mixtures thereof.

The instant invention can be practiced by feeding a distillate boiling range feedstock containing high levels of sulfur and nitrogen to a first hydrodesulfurization reaction stage to remove a substantial amount of the sulfur and nitrogen. Suitable feeds are those containing in excess of about 3,000 wppm sulfur and are typically raw virgin distillates. The feed is hydrodesulfurized in a first stage, which contains one or more reaction zones, in the presence of hydrogen and a first hydrotreating catalyst under hydrodesulfurizing conditions. The product stream is passed to a separation zone wherein a vapor phase stream and a liquid phase stream are produced. The liquid phase product stream is a passed to a second hydrodesulfurization stage, which also contains one or more reaction zones, where it is further hydrodesulfurized in the presence of hydrogen and a second hydrodesulfurization catalyst. The liquid product stream from the second hydrodesulfurization stage is passed to a second separation zone wherein a vapor product stream is collected for further processing or blending. The liquid product stream is passed to a third reaction stage which is operated in the presence of a hydrogenation catalyst. It is within the scope of this invention that at least a portion of the vapor product stream from either or both reaction stages can be recycled to the first reaction stage.

The practice of the present invention encompasses several process schemes. One process scheme is where there are three separate reaction stages, each containing one or more reaction zones, each zone containing a bed of catalyst. The first two reaction stages will contain hydrodesulfurization catalysts and the third reaction stage will contain a hydrogenation catalyst either as the sole catalysts or in combination with the bulk multimetallic catalyst of the present invention. When this process scheme is practiced the feedstock introduced into the first reaction stage is a distillate boiling range feedstock, preferably a distillate boiling range feedstock from an atmospheric distillation tower, such as a raw virgin petroleum distillate. Such a feedstock will contain greater than about 3,000 wppm sulfur and a relatively high nitrogen content. After being hydrodesulfurized in the first hydrodesulfurization stage the feed product stream will contain from about 350 to 600 wppm sulfur. It is preferred that at least one of the reaction zones contain a bed of the bulk multimetallic catalyst of the present invention. For example, the reactor of this first hydrodesulfurization stage can contain a stacked bed arrangement wherein a conventional hydrodesulfurization catalyst comprises one or more reaction zones and the bulk multimetallic catalyst of the present invention comprises the other one or more reaction zones. It is preferred that if a conventional hydrodesulfurization catalyst and a bulk multimetallic catalyst be used the conventional catalyst be in the upstream reaction zone or zones. It is more preferred that all of the reaction zones of this first hydrodesulfurization stage contain the bulk multimetallic catalyst of this invention.

The reaction product is passed to a separation zone where a vapor phase product stream and a liquid phase product stream is produced. The liquid phase product stream that now contains from about 350 to 600 wppm sulfur is introduced into the second hydrodesulfurization stage, which also contains one or more reaction zones. This second hydrodesulfurization stage, like the first, can contain, in one or more of its reaction zone the bulk multimetallic catalyst of this invention. If present, the other catalyst can be a conventional hydrodesulfurization catalyst. The product stream is passed to a second separation zone wherein a vapor phase and liquid phase product streams are produced. The liquid phase product stream will now contain less than about 150 wppm, preferably less than about 100 wppm, and more preferably less than about 50 wppm sulfur. This twice hydrodesulfurized product stream will be passed to a third reaction stage and be reacted in the presence of hydrogen and a catalyst capable of further reducing the sulfur and nitrogen levels and hydrogenating aromatics. The sulfur level of the final product stream will be less than about 10 wppm, preferably less than about 5 wppm, and more preferably less than about 1 wppm sulfur. This third reaction stage will contain, in at least one reaction zone, a hydrogenation catalyst and optionally the bulk multimetallic catalyst of the present invention.

The different types of catalyst arrangements for the three reaction stage process can be:
a) a bulk multimetallic catalyst of this invention in either or both of the first two reaction stages but not the third;
b) a conventional hydrodesulfurization catalyst in the first two reaction stages and only the bulk multimetallic catalyst in the third reaction stage;
c) the bulk multimetallic catalyst in either the first two reaction stages and also in the third reaction stage along with the hydrogenation catalyst, and
d) all three reaction stages have at least one reaction zone containing the bulk multimetallic catalyst.

It is also within the scope of this invention that only two reaction stages be present. In such a case the feedstock to the first reaction stage will be the same feedstock as for the three reaction stage process, except that the product stream from the first stage will contain about 300 to 1,500 wppm, preferably from about 300 to 1,000 wppm, and more preferably from about 300 to 750 wppm sulfur. The second reaction stage will then need to contain both the bulk multimetallic catalyst of this invention as well as an aromatic hydrogenation catalyst. The final product stream will contain less than about 30 wppm, preferably less than about 20 wppm sulfur and a substantially lower level of aromatics.

Non-limiting examples of aromatic hydrogenation catalysts include nickel, cobalt-molybdenum, nickel-molybdenum, and nickel tungsten. Non-limiting examples of noble metal catalysts include those based on platinum and/or palladium, which is preferably supported on a suitable support material, typically a refractory oxide material such as alumina, silica, alumina-silica, kieselguhr, diatomaceous earth, magnesia, and zirconia. Zeolitic supports can also be used. Such catalysts are typically susceptible to sulfur and nitrogen poisoning. The aromatic saturation zone is preferably operated at a temperature from about 40° C. to about 400° C., more preferably from about 260° C. to about 350° C., at a pressure from about 100 psig to about 3,000 psig, preferably from about 200 psig to about 1,200 psig, and at a liquid hourly space velocity (LHSV) of from about 0.3 V/V/Hr. to about 2.0 V/V/Hr.

The hydrotreating catalyst of any one or more of the reaction zones of any one or both of the hydrodesulfurization stages is a bulk multimetallic catalyst comprised of at least one Group VIII non-noble metal and at least two Group VIB metals and wherein the ratio of Group VIB metal to Group VIII non-noble metal is from about 10:1 to about 1:10. It is preferred that the catalyst be a bulk trimetallic catalyst comprised of one Group VIII non-noble metal, preferably Ni or Co and the two Group VIB metals Mo and W. It is preferred that the ratio of Mo to W be about 9:1 to about 1:9.

The preferred bulk trimetallic catalyst compositions used in the practice of the present invention is represented by the formula:

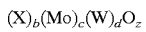

wherein X is one or more a Group VIII non-noble metal, the molar ratio of b:(c+d) is 0.5/1 to 3/1, preferably 0.75/1 to 1.5/1, more preferably 0.75/1 to 1.25/1;

The molar ratio of c:d is preferably >0.01/1, more preferably >0.1/1, still more preferably 1/10 to 10/1, still more preferably 1/3 to 3/1, most preferably substantially equimolar amounts of Mo and W, e.g., 2/3 to 3/2: and z=[2b +6(c+d)]/2.

The essentially amorphous material has a unique X-ray diffraction pattern showing crystalline peaks at d=2.53 Angstroms and d=1.70 Angstroms.

Decomposition of the precursor may be effected at elevated temperatures. e.g., temperatures of at least about 300° C., preferably about 300–450° C. in a suitable atmosphere, e.g., inerts such as nitrogen, argon, or steam, until decomposition is substantially complete, i.e., the ammonium is substantially completely driven off. Substantially complete decomposition can be readily established by thermogravimetric analysis (TGA), i.e., flattening of the weight change curve.

The catalyst compositions used in the practice of the present invention can be prepared by any suitable means.

One such means is a method wherein not all of the metals are in solution. Generally, the contacting of the metal components in the presence of the protic liquid comprises mixing the metal component and subsequently reacting the resulting mixture. It is essential to the solid route that at least one metal components is added at least partly in the solid state during the mixing step and that the metal of at least one of the metal components which have been added at least partly in the solid state, remains at least partly in the solid state during the mixing and reaction step. "Metal" in this context does not mean the metal in its metallic form but present in a metal compound, such as the metal component as initially applied or as present in the bulk catalyst composition.

Generally, during the mixing step either at least one metal component is added at least partly in the solid state and at least one metal component is added in the solute state, or all metal components are added at least partly in the solid state, wherein at least one of the metals of the metal components which are added at least partly in the solid state remains at least partly in the solid state during the entire process of the solid route. That a metal component is added "in the solute state" means that the whole amount of this metal component is added as a solution of this metal component in the protic liquid. That a metal component is added "at least partly in the solid state" means that at least part of the metal component is added as solid metal component and, optionally, another part of the metal component is added as a solution of this metal component in the protic liquid. A typical example is a suspension of a metal component in a protic liquid in which the metal is at least partly present as a solid, and optionally partly dissolved in the protic liquid.

To obtain a bulk catalyst composition with high catalytic activity, it is therefore preferred that the metal components, which are at least partly in the solid state during contacting, are porous metal components. It is desired that the total pore volume and pore size distribution of these metal components is approximately the same as those of conventional hydrotreating catalysts. Conventional hydrotreating catalysts generally have a pore volume of 0.05–5 ml/g, preferably of 0.1–4 ml/g, more preferably of 0.1–3 ml/g and most preferably of 0.1–2 ml/g determined by nitrogen adsorption. Pores with a diameter smaller than 1 nm are generally not present in conventional hydrotreating catalysts. Further, conventional hydrotreating catalysts have generally a surface area of at least 10 m$^2$/g and more preferably of at least 50 m$^2$/g and most preferably of at least 100 m$^2$/g, determined via the B.E.T. method. For instance, nickel carbonate can be chosen which has a total pore volume of 0.19–0.39 ml/g and preferably of 0.24–0.35 ml/g determined by nitrogen adsorption and a surface area of 150–400 m$^2$/g and more preferably of 200–370 m$^2$/g determined by the B.E.T. method. Furthermore these metal components should have a median particle diameter of at least 50 nm, more preferably at least 100 nm. and preferably not more than 5000 $\mu$m and more preferably not more than 3000 $\mu$m. Even more preferably, the median particle diameter lies in the range of 0.1–50 $\mu$m and most preferably in the range of 0.5–50 $\mu$m. For instance, by choosing a metal component which is added at least partly in the solid state and which has a large median particle diameter, the other metal components will only react with the outer layer of the large metal component particle. In this case, so-called "core-shell" structured bulk catalyst particles are obtained.

An appropriate morphology and texture of the metal component can either be achieved by applying suitable preformed metal components or by preparing these metal components by the above-described precipitation under such conditions that a suitable morphology and texture is obtained. A proper selection of appropriate precipitation conditions can be made by routine experimentation.

As has been set out above, to retain the morphology and texture of the metal components which are added at least partly in the solid state, it is essential that the metal of the metal component at least partly remains in the solid state during the whole process of this solid route. It is noted again that it is essential that in no case should the amount of solid metals during the process of the solid route becomes zero. The presence of solid metal comprising particles can easily be detected by visual inspection at least if the diameter of the solid particles in which the metals are comprised is larger than the wavelength of visible light. Of course, methods such as quasi-elastic light scattering (QELS) or near forward scattering which are known to the skilled person can also be used to ensure that in no point in time of the process of the solid route, all metals are in the solute state.

The protic liquid to be applied in the solid or solution route of this invention for preparing catalyst can be any protic liquid. Examples include water, carboxylic acids, and alcohols such as methanol or ethanol. Preferably, a liquid comprising water such as mixtures of an alcohol and water and more preferably water is used as protic liquid in this solid route. Also different protic liquids can be applied simultaneously in the solid route. For instance, it is possible to add a suspension of a metal component in ethanol to an aqueous solution of another metal component. In some cases, a metal component can be used which dissolves in its own crystal water. The crystal water serves as protic liquid in this case.

The Group VIB metal generally comprises chromium, molybdenum, tungsten, or mixtures thereof. Suitable Group VIII non-noble metals are, e.g., iron, cobalt, nickel, or mixtures thereof. Preferably, a combination of metal components comprising nickel, molybdenum and tungsten or nickel, cobalt, molybdenum and tungsten is applied in the process of the solid route. If the protic liquid is water, suitable nickel components which are at least partly in the solid state during contacting comprise water-insoluble nickel components such as nickel carbonate, nickel hydroxide, nickel phosphate, nickel phosphite, nickel formate, nickel sulfide, nickel molybdate, nickel tungstate, nickel oxide, nickel alloys such as nickel-molybdenum alloys, Raney nickel, or mixtures thereof. Suitable molybdenum components, which are at least partly in the solid state during contacting, comprise water-insoluble molybdenum components such as molybdenum (di- and tri) oxide, molybdenum carbide, molybdenum nitride, aluminum molybdate, molybdic acid (e.g. $H_2MoO_4$), molybdenum sulfide, or mixtures thereof. Finally, suitable tungsten components which are at least partly in the solid state during contacting comprise tungsten di- and trioxide, tungsten sulfide ($WS_2$ and $WS_3$), tungsten carbide, tungstic acid (e.g. $H_2WO_4$—$H_2O$, $H_2W_4O_{13}$—$9H_2O$), tungsten nitride, aluminum tungstate (also meta-, or polytungstate) or mixtures thereof. These components are generally commercially available or can be prepared by, e.g., precipitation, e.g., nickel carbonate can be prepared from a nickel chloride, sulfate, or nitrate solution by adding an appropriate amount of sodium carbonate. It is generally known to the skilled person to choose the precipitation conditions in such a way as to obtain the desired morphology and texture.

In general, metal components, which mainly contain C, O, and/or H besides the metal, are preferred because they are less detrimental to the environment. Nickel carbonate is a preferred metal component to be added at least partly in the solid state because when nickel carbonate is applied, $CO_2$ evolves and positively influences the pH of the reaction mixture. Further, due to the transformation of carbonate into $CO_2$, the carbonate does not end up in the wastewater.

Preferred nickel components which are added in the solute state are water-soluble nickel components, e.g. nickel nitrate, nickel sulfate, nickel acetate, nickel chloride, or mixtures thereof. Preferred molybdenum and tungsten components which are added in the solute state are water-soluble molybdenum and tungsten components such as alkali metal or ammonium molybdate (also peroxo-, di-, tri-, tetra-, hepta-, octa-, or tetradecamolybdate), Mo—P heteropolyanion compounds, Wo—Si heteropolyanion compounds, W—P heteropolyanion compounds, W—Si heteropolyanion compounds, Ni—Mo—W heteropolyanion compounds, Co—Mo—W heteropolyanion compounds, alkali metal or ammonium tungstates (also meta-, para-, hexa-, or polytungstate), or mixtures thereof.

Preferred combinations of metal components are nickel carbonate, tungstic acid and molybdenum oxide. Another preferred combination is nickel carbonate, ammonium dimolybdate and ammonium metatungstate. It is within the scope of the skilled person to select further suitable combinations of metal components. It must be noted that nickel carbonate always comprises a certain amount of hydroxy-groups. It is preferred that the amount of hydroxy-groups present in the nickel carbonate be high.

An alternative method of preparing the catalysts used in the practice of the present invention is to prepare the bulk catalyst composition by a process comprising reacting in a reaction mixture a Group VIII non-noble metal component in solution and a Group VIB metal component in solution to obtain a precipitate. As in the case of the solid route, preferably, one Group VIII non-noble metal component is reacted with two Group VIB metal components. The molar ratio of Group VIB metals to Group VIII non-noble metals applied in the process of the solution route is preferably the same as described for the solid route. Suitable Group VIB and Group VIII non-noble metal components are, e.g. those water-soluble nickel, molybdenum and tungsten components described above for the solid route. Further Group VIII non-noble metal components are, e.g., cobalt or iron components. Further Group VIB metal components are, e.g. chromium components. The metal components can be added to the reaction mixture in solution, suspension or as such. If soluble salts are added as such, they will dissolve in the reaction mixture and subsequently be precipitated. Suitable Group VIB metal salts which are soluble in water are ammonium salts such as ammonium dimolybdate, ammonium tri-, tetra- hepta-, octa-, and tetradeca-molybdate, ammonium para-, meta-, hexa-, and polytungstate, alkali metal salts, silicic acid salts of Group VIB metals such as molybdic silicic acid, molybdic silicic tungstic acid, tungstic acid, metatungstic acid, pertungstic acid, heteropolyanion compounds of Mo—P, Mo—Si, W—P, and W—Si. It is also possible to add Group VIB metal-containing compounds which are not in solution at the time of addition, but where solution is effected in the reaction mixture. Examples of these compounds are metal compounds which contain so much crystal water that upon temperature increase they will dissolve in their own metal water. Further, non-soluble metal salts may be added in suspension or as such, and solution is effected in the reaction mixture. Suitable non-soluble metals salts are heteropolyanion compounds of Co—Mo—W (moderately soluble in cold water), heteropolyanion compounds of Ni—Mo—W (moderately soluble in cold water).

The reaction mixture is reacted to obtain a precipitate. Precipitation is effected by adding a Group VIII non-noble metal salt solution at a temperature and pH at which the Group VIII non-noble metal and the Group VIB metal precipitate, adding a compound which complexes the metals and releases the metals for precipitation upon temperature increase or pH change or adding a Group VIB metal salt solution at a temperature and pH at which the Group VIII non-noble metal and Group VIB metal precipitate, changing the temperature, changing the pH, or lowering the amount of the solvent. The precipitate obtained with this process appears to have high catalytic activity. In contrast to the conventional hydroprocessing catalysts, which usually comprise a carrier impregnated with Group VIII non-noble metals and Group VIB metals, said precipitate can be used without a support. Unsupported catalyst compositions are usually referred to as bulk catalysts. Changing the pH can be done by adding base or acid to the reaction mixture, or adding compounds, which decompose upon temperature, increase into hydroxide ions or $H^+$ ions that respectively increase or decrease the pH. Examples of compounds that decompose upon temperature increase and thereby Increase or decrease the pH are urea, nitrites, ammonium cyanate, ammonium hydroxide, and ammonium carbonate.

In an illustrative process according to the solution route, solutions of ammonium salts of a Group VIB metal are made and a solution of a Group VIII non-noble metal nitrate is made. Both solutions are heated to a temperature of approximately 90° C. Ammonium hydroxide is added to the Group VIB metal solution. The Group VIII non-noble metal solution is added to the Group VIB metal solution and direct precipitation of the Group VIB and Group VIII non-noble metal components occurs. This process can also be conducted at lower temperature and/or decreased pressure or higher temperature and/or increased pressure.

In another illustrative process according to the solution route, a Group VIB metal salt, a Group VIII metal salt, and ammonium hydroxide are mixed in solution together and heated so that ammonia is driven off and the pH is lowered to a pH at which precipitation occurs. For instance when nickel, molybdenum, and tungsten components are applied, precipitation typically occurs at a pH below 7.

Independently from whether the solid or solution route is chosen the resulting bulk catalyst composition preferably comprises and more preferably consists essentially of bulk catalyst particles having the characteristics of the bulk catalyst particles described under the heading "Catalyst compositions of the invention."

The bulk catalyst composition can generally be directly shaped into hydroprocessing particles. If the amount of liquid of the bulk catalyst composition is so high that it cannot be directly subjected to a shaping step, a solid liquid separation can be performed before shaping. Optionally the bulk catalyst composition, either as such or after solid liquid separation, can be calcined before shaping.

The median diameter of the bulk catalyst particles is at least 50 nm, more preferably at least 100 nm, and preferably not more than 5000 $\mu$m and more preferably not more than 3000 $\mu$m. Even more preferably, the median particle diameter lies in the range of 0.1–50 $\mu$m and most preferably in the range of 0.5–50 $\mu$m.

If a binder material is used in the preparation of the catalyst composition it can be any material that is conventionally applied as a binder in hydroprocessing catalysts. Examples include silica, silica-alumina, such as conventional silica-alumina, silica-coated alumina and alumina-coated silica, alumina such as (pseudo)boehmite, or gibbsite, titania, zirconia, cationic clays or anionic clays such as saponite, bentonite, kaoline, sepiolite or hydrotalcite, or mixtures thereof. Preferred binders are silica, silica-alumina, alumina, titanic, zirconia, or mixtures thereof. These binders may be applied as such or after peptization. It is also possible to apply precursors of these binders that, during the process of the invention are converted into any of the above-described binders. Suitable precursors are, e g., alkali metal aluminates (to obtain an alumina binder), water glass (to obtain a silica binder), a mixture of alkali metal aluminates and water glass (to obtain a silica alumina binder), a mixture of sources of a di-, tri-, and/or tetravalent metal such as a mixture of water-soluble salts of magnesium, aluminum and/or silicon (to prepare a cationic clay and/or anionic clay), chlorohydrol, aluminum sulfate, or mixtures thereof.

If desired, the binder material may be composited with a Group VIB metal and/or a Group VIII non-noble. metal, prior to being composited with the bulk catalyst composition and/or prior to being added during the preparation thereof. Compositing the binder material with any of these metals may be carried out by impregnation of the solid binder with these materials. The person skilled in the art knows suitable impregnation techniques. If the binder is peptized, it is also possible to carry out the peptization in the presence of Group VIB and/or Group VIII non-noble metal components.

If alumina is applied as binder, the surface area preferably lies in the range of 100–400 m$^2$/g, and more preferably 150–350 m$^2$/g, measured by the B.E.T. method. The pore volume of the alumina is preferably in the range of 0.5–1.5 ml/g measured by nitrogen adsorption.

Generally, the binder material to be added in the process of the invention has less catalytic activity than the bulk catalyst composition or no catalytic activity at all. Consequently, by adding a binder material, the activity of the bulk catalyst composition may be reduced. Therefore, the amount of binder material to be added in the process of the invention generally depends on the desired activity of the final catalyst composition. Binder amounts from 0–95 wt. % of the total composition can be suitable, depending on the envisaged catalytic application. However, to take advantage of the resulting unusual high activity of the composition of the present invention, binder amounts to be added are generally in the range of 0.5–75 wt. % of the total composition.

The catalyst composition can be directly shaped. Shaping comprises extrusion, pelletizing, beading, and/or spray drying. It must be noted that if the catalyst composition is to be applied in slurry type reactors, fluidized beds. moving beds, expanded beds, or ebullating beds spray drying or beading is generally applied for fixed bed applications, generally, the catalyst composition is extruded, pelletized and/or beaded. In the latter case, prior to or during the shaping step, any additives that are conventionally used to facilitate shaping can be added. These additives may comprise aluminum stearate, surfactants, graphite or mixtures thereof. These additives can be added at any stage prior to the shaping step. Further, when alumina is used as a binder, it may be desirable to add acids prior to the shaping step such as nitric acid to increase the mechanical strength of the extrudates.

It is preferred that a binder material is added prior to the shaping step. Further, it is preferred that the shaping step is carried out in the presence of a liquid, such as water. Preferably, the amount of liquid in the extrusion mixture, expressed as LOI is in the range of 20–80%.

The resulting shaped catalyst composition can, after an optional drying step, be optionally calcined. Calcination however is not essential to the process of the invention. If a calcination is carried out in the process of the invention, it can be done at a temperature of, e.g., from 100°–600° C. and preferably 350° to 500° C. for a time varying from 0 5 to 48 hours. The drying of the shaped particles is generally carried out at temperatures above 100° C.

In a preferred embodiment of the invention, the catalyst composition is subjected to spray drying, (flash) drying, milling, kneading, or combinations thereof prior to shaping. These additional process steps can be conducted either before or after a binder is added, after solid-liquid separation, before or after calcination and subsequent to re-wetting. It is believed that by applying any of the above-described techniques of spray drying, (flash) drying, milling, kneading, or combinations thereof, the degree of mixing between the bulk catalyst composition and the binder material is improved. This applies to both cases where the binder material is added before or after the application of any of the above-described methods. However, it is generally preferred to add the binder material prior to spray drying and/or any alternative technique. If the binder is added subsequent to spray drying and/or any alternative technique, the resulting composition is preferably thoroughly mixed by any conventional technique prior to shaping. An advantage of, e.g., spray drying is that no wastewater streams are obtained when this technique is applied.

Furthermore, a cracking component may be added during catalyst preparation. The cracking component may serve as an isomerization enhancer. The cracking component can be any conventional cracking component such as cationic clays, anionic clays, zeolites such as ZSM-5, (ultra-stable) zeolite Y, zeolite X, ALPO's. SAPO's, amorphous cracking components such as silica-alumina, or mixtures thereof. It will be clear that some materials may act as a binder and a cracking component at the same time. For instance, silica-alumina may have at the same time a cracking and a binding function.

If desired, the cracking component may be composited with a Group VIB metal and/or a Group VIII non-noble metal prior to being composited with the bulk catalyst composition and/or prior to being added during the preparation thereof. Compositing the cracking component with any of these metals may be carried out by impregnation of the cracking component with these materials.

The cracking component, which can comprise about 0–80 wt. %, based on the total weight of the catalyst, can be added at any stage of the process of the present invention prior to the shaping step. However, it is preferred to add the cracking component during the compositing step (ii) with the binder.

Generally, it depends on the envisaged catalytic application of the final catalyst composition which of the above-described cracking components is added. A zeolite is preferably added if the resulting composition shall be applied in hydrocracking or fluid catalytic cracking. Other cracking components such as silica-alumina or cationic clays are preferably added if the final catalyst composition shall be used in hydrotreating applications. The amount of cracking material that is added depends on the desired activity of the final composition and the application envisaged and thus may vary from 0–80 wt. %, based on the total weight of the catalyst composition.

If desired, further materials can be added in addition to the metal components already added. These materials include any material that is added during conventional hydroprocessing catalyst preparation. Suitable examples are phosphorus compounds, boron compounds, fluorine-containing compounds, additional transition metals, rare earth metals, fillers, or mixtures thereof.

Suitable phosphorus compounds include ammonium phosphate, phosphoric acid, or organic phosphorus compounds. Phosphorus compounds can be added at any stage of the process of the present invention prior to the shaping step and/or subsequent to the shaping step. If the binder material is peptized, phosphorus compounds can also be used for peptization. For instance, the binder can be peptized by contacting the binder with phosphoric acid or with a mixture of phosphoric and nitric acid.

Suitable additional transition metals are, e.g., rhenium, ruthenium, rhodium, iridium, chromium, vanadium, iron, cobalt, platinum, palladium, cobalt, nickel, molybdenum, or tungsten. Nickel, molybdenum and tungsten can be applied in the form of any of the water-insoluble nickel, molybdenum and/or tungsten components that are described above for the solid route. These metals can be added at any stage of the process of the present invention prior to the shaping step. Apart from adding these metals during the process of the invention, it is also possible to composite the final catalyst composition therewith. It is, e.g., possible to impregnate the final catalyst composition with an impregnation solution comprising any of these metals.

The processes of the present invention for preparing the bulk catalyst compositions may further comprise a sulfidation step. Sulfidation is generally carried out by contacting the catalyst composition or precursors thereof with a sulfur containing compound such as elementary sulfur, hydrogen sulfide or polysulfides. The sulfidation can generally be carried out subsequently to the preparation of the bulk catalyst composition but prior to the addition of a binder material, and/or subsequently to the addition of the binder material but prior to subjecting the catalyst composition to spray drying and/or any alternative method, and/or subsequently to subjecting the composition to spray drying and/or any alternative method but prior to shaping, and/or subsequently to shaping the catalyst composition. It is preferred that the sulfidation is not carried out prior to any process step that reverts the obtained metal sulfides into their oxides. Such process steps are, e.g., calcination or spray drying or any other high temperature treatment in the presence of oxygen. Consequently, if the catalyst composition is subjected to spray drying and/or any alternative technique, the sulfidation should be carried out subsequent to the application of any of these methods.

Additionally to, or instead of, a sulfidation step, the bulk catalyst composition may be prepared from at least one metal sulfide. If, e.g. the solid route is applied in step (i), the bulk catalyst component can be prepared form nickel sulfide and/or molybdenum sulfide and/or tungsten sulfide.

If the catalyst composition is used in a fixed bed processes, the sulfidation is preferably carried out subsequent to the shaping step and, if applied. subsequent to the last calcination step. Preferably, the sulfidation is carried out ex situ, i.e., the sulfidation is carried out in a separate reactor prior to loading the sulfided catalyst composition into the hydroprocessing unit. Furthermore, it is preferred that the catalyst composition is both sulfided ex situ and in situ.

One or more of the reaction zones of any or both of the hydrodesulfurization stages, may contain a conventional hydrodesulfurization catalyst. Suitable conventional hydrodesulfurization catalysts for use in the present invention includes those that are comprised of at least one Group VIII metal, preferably Fe, Co or Ni, more preferably Co and/or Ni, and most preferably Co; and at least one Group VI metal, preferably Mo or W, more preferably Mo, on a relatively high surface area support material, preferably alumina. Other suitable hydrodesulfurization catalyst supports include zeolites, amorphous silica-alumina, and titania-alumina. Noble metal catalysts can also be employed, preferably when the noble metal is selected from Pd and Pt. It is within the scope of the present invention that more than one type of hydrodesulfurization catalyst be used in the same reaction vessel. The Group VIII metal is typically present in an amount ranging from about 2 to 20 wt. %, preferably from about 4 to 12%. The Group VI metal will typically be present in an amount ranging from about 5 to 50 wt. %, preferably from about 10 to 40 wt. %, and more preferably from about 20 to 30 wt. %. All metal weight percents are on support. By "on support" we mean that the percents are based on the weight of the support. For example, if the support were to weigh 100 g. then 20 wt. % Group VIII metal would mean that 20 g. of Group VIII metal was on the support.

It has been found that in this case, the bulk catalyst particles are sintering-resistant. Thus the active surface area of the bulk catalyst particles is maintained during use. The molar ratio of Group VIB to Group VIII non-noble metals ranges generally from 10:1–1:10 and preferably from 3:1–1:3. In the case of a core-shell structured particle, these ratios of course apply to the metals contained in the shell. If more than one Group VIB metal is contained in the bulk catalyst particles, the ratio of the different Group VIB metals is generally not critical. The same holds when more than one Group VIII non-noble metal is applied. In the case where molybdenum and tungsten are present as Group VIB metals, the molybenum:tungsten ratio preferably lies in the range of 9:1–1:9. Preferably the Group VIII non-noble metal comprises nickel and/or cobalt. It is further preferred that the Group VIB metal comprises a combination of molybdenum and tungsten. Preferably, combinations of nickel/molybdenum/tungsten and cobalt/molybdenum/tungsten and nickel/cobalt/molybdenum/tungsten are used. These types of precipitates appear to be sinter-resistant. Thus, the active surface area of the precipitate is retained during use. The metals are preferably present as oxidic compounds of the corresponding metals, or if the catalyst composition has been sulfided, sulfidic compounds of the corresponding metals.

Preferably the particles have a surface area of at least 50 $m^2/g$ and more preferably of at least 100 $m^2/g$ measured via the B.E.T. method. It is furthermore preferred that the particles comprise 50–100 wt. %, and even more preferably 70–100 wt. % of at least one Group VIII non-noble metal and at least one Group VIB metal, based on the total weight of the particles, calculated as metal oxides. The amount of Group VIB and Group VIII non-noble metals can easily be determined via TEM-EDX.

It is desired that the pore size distribution of the particles is approximately the same as the one of conventional hydrotreating catalysts. More in particular, these particles have preferably a pore volume of 0.05–5 ml/g, more preferably of 0.1–4 ml/g, still more preferably of 0.1–3 ml/g and most preferably 0.1–2 ml/g determined by nitrogen adsorption. Preferably, pores smaller than 1 nm are not present. Furthermore these particles preferably have a median diameter of at least 50 nm, more preferably at least 100 nm, and preferably not more than 5000 μm and more preferably not more than 3000 μm. Even more preferably, the median particle diameter lies in the range of 0.1–50 μm and most preferably in the range of 0 5–50 μm.

The surface area of the catalyst composition preferably is at least 40 $m^2/g$, more preferably at least 80 $m^2/g$ and most preferably at least 120 $m^2/g$. The total pore volume of the catalyst composition is preferably at least 0.05 ml/g and more preferably at least 01 ml/g as determined by water porosimetry. To obtain catalyst compositions with high mechanical strength, it may be desirable that the catalyst composition of the invention has a low macroporosity.

It was found that the bulk catalyst particles have a characteristic X-ray diffraction pattern which differs from catalysts obtained by co-mixing and conventional hydroprocessing catalysts obtained by impregnation. The X-ray diffraction pattern of the bulk catalyst particles comprises, and preferably essentially consists of, peaks characteristic to the reacted metal components. If, e.g., nickel hydroxy-carbonate has been contacted with a molybdenum and tungsten component as described above, the resulting bulk catalyst particles are characterized by an X-ray diffraction pattern which comprises peaks at d values of (4.09 Å), 2.83 Å, 2.53 Å, 2.32 Å, 2.23 Å, 1.70 Å, (1.54 Å), 1.47 Å. Values in brackets indicate that the corresponding peaks are rather broad and/or have a low intensity or are not distinguished at all. The term "the X-ray diffraction pattern essentially consists of" these peaks means that apart from these peaks, there are essentially no further peaks contained in the diffraction pattern. The precipitate for catalyst obtained by the solution route has a characteristic X-ray diffraction pattern which differs from catalyst obtained by co-mixing and conventional hydroprocessing catalysts obtained by impregnation. For instance the X-ray diffraction pattern of a Ni—Mo—W precipitate as prepared by the solution route has peaks at d values of 2.52 Å, 1.72 Å and 1.46 Å.

Also as previously stated, the catalyst composition may comprise conventional hydroprocessing catalysts. The binder materials and cracking components of the conventional hydroprocessing catalyst generally comprise any of the above-described binder materials and cracking components. The hydrogenation metals of the conventional hydroprocessing catalyst generally comprise Group VIB and Group VIII non-noble metals such as combinations of nickel or cobalt with molybdenum or tungsten. Suitable conventional hydroprocessing catalysts are, e.g.. hydrotreating catalysts. These catalysts can be in the spent, regenerated, or fresh state.

As will be clear from the above, it is possible to add the Group VII non-noble metal containing compound and the Group VIB metal-containing compound in various ways, at various temperatures and pHs, in solution, in suspension, and as such, simultaneously and sequentially.

The precursor compound can also be readily prepared by one of several methods, including a variation of the boiling decomposition method used by Teichner and Astier in which a tungsten compound is added to the initial mixture of a molybdenum salt, a nickel salt and ammonium hydroxide. Direct precipitation and pH controlled precipitation may also be used to prepare the precursor compound. In all cases, however, water soluble salts of nickel, molybdenum and tungsten are employed.

Preferably, the molybdenum and tungsten salts are ammonium compounds, e.g., ammonium molybdate, ammonium metatungstate, while the nickel salt may be the nitrate or hydrated nitrates.

The decomposed precursor can be sulfided or pre-sulfided by a variety of known methods. For example, the decomposition product can be contacted with a gas comprising $H_2S$ and hydrogen, e.g., 10% $H_2S/H_2$, at elevated temperatures for a period of time sufficient to sulfide the decomposition product, usually at the point of $H_2S$ breakthrough in the exit gas. Sulfiding can also be effected, in situ, by passing a typical feedstock containing sulfur over the decomposition product.

Process conditions applicable for the use of the catalysts described herein may vary widely depending on the feedstock to be treated. Thus, as the boiling point of the feed increases, the severity of the conditions will also increase. The following table serves to illustrate typical conditions for a range of feeds.

| FEED | TYPICAL BOILING RANGE ° C. | TEMP. ° C. | PRESS. BAR | SPACE VELOCITY V/V/HR | $H_2$ GAS RATE SCF/B |
|---|---|---|---|---|---|
| Naphtha | 25–210 | 100–370 | 10–60 | 0.5–10 | 100–2,000 |
| Diesel | 170–350 | 200–400 | 15–110 | 0.5–4 | 500–6,000 |
| Heavy gas oil | 2325–475 | 260–430 | 15–170 | 0.3–2 | 1000–6,000 |
| lube oil | 290–550 | 200–450 | 6–210 | 0.2–5 | 100–10,000 |
| Residuum | 10–50% > 575 | 340–450 | 65–1100 | 0.1–1 | 2,000–10,000 |

The following examples will serve to illustrate, but not limit, this invention.

EXAMPLE 1

Preparation of $NH_4$—Ni—Mo—O Phase (Boiling Decomposition as Per Teichner and Astier Procedure)

In a 1 liter flask, 26.5 g ammonium molybdate (0.15 moles Mo) and 43.6 g nickel nitrate hexahydrate (0.15 moles Ni) were dissolved in 300 cc of water so that the resulting pH equaled 4.3. To this solution, a concentrated $NH_4OH$ solution was added. At first, a precipitate formed which on further addition of $NH_4OH$ dissolved to give a clear blue solution with a pH of 8.3, and additional $NH_4OH$ (~250 cc) was added until a pH of 10 was reached. The solution was heated to 90° C. for 3 h during which ammonia gas evolved and a green precipitate formed. The final pH lay between 6.8 and 7. The suspension was cooled to room temperature, filtered, washed with water and dried at 120° C. overnight. About 18.6 g of material was obtained. The sample analyzed for Ni at 26.6 wt. % and Mo at 34 wt. %. The X-ray diffraction spectra of the phase matches the pattern reported by Teichner and Astier.

EXAMPLE 2

Preparation of $NH_4$—Ni—$Mo_{0.5}W_{0.5}$—O by Boiling Decomposition

In a 1 liter flask, 13.2 g ammonium molybdate (0.075 moles Mo), 18.7 g ammonium metatungstate (0.075 moles W) and 43.6 g nickel nitrate hexahydrate (0.15 moles Ni)

were dissolved in 300 cc of water so that the resulting pH equaled 4.3. To this solution, a concentrated $NH_4OH$ solution (~600 cc) was added until the pH reached 10. At this point, some precipitate remained. The solution was refluxed at ~100° C. for 3 h. During this heating, the precipitate dissolved to give a clear blue solution and on further heating, a green precipitate formed. The heating was continued until the pH reached between 6.8 and 7. The suspension was cooled to room temperature, filtered, washed with water and dried at 120° C. overnight. 18 grams of material is obtained. The X-ray diffraction spectra of the phase is given in FIG. 1 showing an amorphous background with the two largest peaks at d=2.53 and 1.70 Å.

EXAMPLE 3

Preparation of $NH_4$—Ni—$Mo_{0.5}W_{0.5}$—O by Direct Precipitation

In a 1 liter flask, 17.65 g of ammonium molybdate (0.1 mole Mo) and 24.60 g of ammonium metatungstate (0.1 mole W) were dissolved in 800 cc of water giving a solution pH of ~5.2. To this solution 0.4 moles of $NH_4OH$ (~30 cc) was added, raising the pH to ~9.8 (solution A). This solution was warmed to 90° C. A second solution was prepared by adding 58.2 g of nickel nitrate, (0.2 moles Ni) which was dissolved in 50 cc of water (solution B) and maintained at 90° C. This solution was added dropwise at a rate of 7 cc/min into the ammonium molybdate/ammonium metatungstate solution. A precipitate begins to form after ¼ of the solution was added. This suspension which was at a pH ~6.5 was stirred for 30 minutes while the temperature was maintained at 90° C. The material was filtered hot, washed with hot water, and dried at 120° C. Approximately 38 g of material was recovered.

EXAMPLE 4

Preparation of $NH_4$—Ni—$Mo_{0.5}W_{0.5}$—O by Controlled pH Precipitation

Two solutions were prepared with the same amounts of nickel, tungsten, molybdenum and ammonium hydroxide are described in Example 3 (solutions A and B) except that each solution contained about 700 cc of water. The two solutions were added into a separate vessel initially containing 400 cc of water held at 90° C. Solution B (the acidic solution) was pumped into the vessel at a constant rate of ~15 cc/min, while solution A is added through a separate pump which is under feedback PC control and set to maintain the pH at 6.5. On mixing the two solutions a precipitate forms. The slurry was stirred at 90° C. for 30 minutes, filtered hot, washed with hot water, and dried at 120° C.

EXAMPLE 5

Catalytic Evaluation Using Dibenzothiophene (DBT)

1.5–2 g of the catalysts of Examples 1–4 were placed in a quartz boat which was in turn inserted into a horizontal quartz tube and placed into a Lindberg furnace. The temperature was raised to 370° C. in about one hour with $N_2$ flowing at 50 cc/m, and the flow continued for 1.5 h at 370° C. $N_2$ was switched off and 10% $H_2S/H_2$ then added to the reactor at 20 cc/m, the temperature increased to 400° C., and held there for 2 hours. The heat was then shut off and the catalyst cooled in flowing $H_2S/H_2$ to 70° C., at which point this flow was discontinued and $N_2$ was added. At room temperature, the quartz tube was removed and the material transferred into a $N_2$ purged glove box. Catalysts were evaluated in a 300 cc modified Carberry batch reactor designed for constant hydrogen flow. The catalyst was pilled and sized to 20/40 mesh and one gram was loaded into a stainless steel basket, sandwiched between a layer of nullite beads. 100 cc of liquid feed, containing 5 wt. % Dibenzothiophene in decalin was added to the autoclave. A hydrogen flow of 100 cc/min was passed through the reactor and the pressure was maintained at 3150 kPa using a back pressure regulator. The temperature was raised to 350° C. at 5–6 deg/min and run until either 50% DBT was converted or until 7 hours was reached. A small aliquot of product was removed every 30 minutes and analyzed by GC. Rate constants for the overall conversion as well as the conversion to the reaction products biphenyl (BP) and cyclohexylbenzene (CHB) were calculated as described by M. Daage and R. R. Chianelli [J. Cat. 149, 414–27 (1994)] and are shown in Table 1. As described in that article, high selectivities to cyclohexylbenzene relative to BP during the desulfurization reaction are a good indication of a catalyst with high hydrodenitrogenation activity, whereas high selectivities of BP relative to CHB indicates a catalyst with high hydrodesulfurization activity.

The results show that partial substitution of tungsten for molybdenum results in catalysts that are substantially higher for DBT conversion. A standard supported Ni—Mo on $Al_2O_3$ catalyst is also shown for comparison. The high CHB/BP ratio suggests that the catalysts are active for HDN.

TABLE 1

Comparison of Activity in DBT Conversion Tests With Tungsten Addition by Different Preparation Schemes

| Catalyst | preparation technique | example # | $K_{total}$ @ 350° C. | CHB/BP @ 350° C. |
|---|---|---|---|---|
| $NH_4$—Ni—Mo—O | boiling decomposition | 1 | 106 | 10.4 |
| $NH_4$—Ni—$Mo_{.5}W_{.5}$—O | boiling decomposition | 2 | 171 | 10.2 |
| $NH_4$—Ni—$MO_{.5}W_{.5}$—O | direct precipitation | 3 | 167 | 12.4 |
| $NH_4$—Ni—$Mo_{.5}W_{.5}$—O | controlled pH preparation | 4 | 181 | 12.0 |
| $Ni.Mo/Al_2O_3$ | impregnation | | 129 | 6.4 |

EXAMPLE 6

A series of catalysts were prepared in accordance with the general preparation scheme of example 2 (i.e., boiling decomposition) but varying the Mo and W relative ratios by changing the amount of ammonium molybdate and ammonium metatungstate added to the solutions. Decomposition was effected as described in Example 5. The catalysts so prepared are shown in Table 2 along with their catalytic activities for DBT measured as described in Example 5.

TABLE 2

Comparison of Activity in DBT Conversion Tests with Variation in Relative W and Mo content

| Catalyst | Sample | ammonium molybdate (g) | ammonium metatungstate (g) | nickel nitrate hexahydrate (g) | $K_{total}$ @ 350° C. | CHB/BP @ 350° C. |
|---|---|---|---|---|---|---|
| $NH_4$—NiW—O | 18983–97 | 0 | 36.95 | 43.62 | 128 | 11.3 |
| $NH_4$—$NiMo_{.1}W_{.9}$—O | 18983–125 | 2.65 | 33.62 | 43.62 | 132 | 14.1 |
| $NH_4$—$NiMo_{.3}W_{.7}$—O | 18983–101 | 7.94 | 25.87 | 43.62 | 154 | 11.6 |
| $NH_4$—$NiMo_{.5}W_{.5}$—O | 18357–109 | 13.17 | 18.74 | 43.62 | 171 | 10.2 |
| $NH_4$—$NiMo_{.7}W_{.3}$—O | 18983–95 | 18.54 | 11.09 | 43.62 | 158 | 11.5 |
| $NH_4$—$NiMo_{.9}W_{.1}$—O | 18983–92 | 23.83 | 3.69 | 43.62 | 141 | 10.5 |

The data show that the most active catalyst contains an approximately equimolar mixture of tungsten and molybdenum.

EXAMPLE 7

A series of catalysts were prepared as described in Example 3 (direct precipitation) in which equimolar mixtures of Mo and W were precipitated but the nickel content was varied. Decomposition was effected as described in Example 5. The catalysts so prepared are shown in Table 3 alone with their catalytic activities for DBT measured as described in example 5.

EXAMPLE 8

A series of catalysts were prepared in which the quantity of $NH_4OH$ used in the preparation was varied. The catalysts were prepared in accordance to the procedure described in Example 3 except that the amount of $NH_4OH$ in solution A was varied to change to $NH_4OH$/Ni molar ratio when the two solutions were mixed. Decomposition was effected as described in Example 5. The catalysts so prepared are shown in Table 4 along with their catalytic activities for DBT measured as described in Example 5.

TABLE 3

Variation of Nickel Content in $NH_4$—Ni—$Mo_{.5}W_{.5}$—O Catalysts

| Catalyst | Sample | ammonium molybdate (g) | ammonium metatungstate (g) | nickel nitrate hexahydrate (g) | $K_{total}$ @ 350° C. | CHB/BP @ 350° C. |
|---|---|---|---|---|---|---|
| $NH_4$—$Ni_{0.75}Mo_{.5}W_{.5}$—O | 19086–110 | 17.65 | 24.6 | 43.65 | 171 | 13.0 |
| $NH_4$—$Ni_{1.0}Mo_{.5}W_{.5}$—O | 19086–82 | 17.65 | 24.6 | 58.2 | 167 | 12.4 |
| $NH_4$—$Ni_{1.25}Mo_{.5}W_{.5}$—O | 19086–111 | 17.65 | 24.6 | 72.75 | 174 | 11.0 |
| $NH_4$—$Ni_{1.5}Mo_{.5}W_{.5}$—O | 19086–112 | 17.65 | 24.6 | 87.3 | 148 | 9.55 |

Catalytic performance does not change substantially with variations in Ni from 0.75 to 1.5, although K appears to go through a maximum at about 1.25 Ni.

TABLE 4

Variation in $NH_4OH$ Addition to Preparation

| Catalyst $NH_4OH$/Ni mole ratio | Sample | ammonium molybdate (g) | ammonium metatungstate (g) | nickel nitrate hexahydrate (g) | $cm^3$ conc $NH_4OH$ | $K_{total}$ @ 350° C. | $K_{CHB/BP}$ @ 350° C. |
|---|---|---|---|---|---|---|---|
| 1:2 | 19086–96 | 17.65 | 24.6 | 43.65 | 6.8 | 102 | 10.5 |
| 1:1 | 19086–97 | 17.65 | 24.6 | 58.2 | 14 | 137 | 10.4 |
| 2:1 | 19086–82 | 17.65 | 24.6 | 72.75 | 30 | 167 | 12.4 |
| 3:1 | 19086–104 | 17.65 | 24.6 | 87.3 | 41 | 164 | 11.4 |
| 4:1 | 19086–106 | 17.65 | 24.6 | 87.3 | 55 | 161 | 12.1 |

While decomposition of the precursor compound will drive off most, if not all, of the ammonium portion of the precursor, the preparation of the precursor and the catalytic utility of the decomposition product can be affected by the amount of $NH_4OH$ employed. Thus, the effectiveness of the decomposition product as a catalyst is enhanced when the $NH_4OH/Ni$ ratio in the preparation of the precursor compound is from about 1:1 to about 4:1, preferably about 1.5:1 to about 4:1, and more preferably about 2:1 to about 4:1. While not wishing to be bound by any particular theory or mechanism, there is some evidence the $NH_4OH/Ni$ ratio causes the Ni—M—W—O phase to change in the decomposition product.

EXAMPLE 9

The catalysts of examples 1 and 2 were compared against standard supported Ni—Mo catalysts for the conversion of a LSADO (low sulfur auto diesel oil feed). This feed contained 510 wppm sulfur, 50 wppm nitrogen, and 30.6% aromatics with a gravity of 39.8° API. The catalysts were tested at 579° F., 650 psig of $H_2$, and 1850 SCFB/B of $H_2$. The relative activities of the different catalysts are summarized in Table 5.

TABLE 5

Relative Hydrotreating Activities on LSADO Feed

| Catalyst | Relative Volumetric HDS Activity | Relative Volumetric HDN Activity |
| --- | --- | --- |
| $NiMo/Al_2O_3$ | 1 | 1 |
| $NH_4$—NiMo—O | 0.25 | 0.50 |
| $NH_4$—$Ni_{1.0}Mo_{0.5}W_{0.5}$—O | 1.4 | 2.05 |

The $NiMo/Al_2O_3$ catalyst is a standard HDN/HDS catalyst, the $NH_4$—Ni—Mo phase is the bulk phase with no tungsten, and the $NH_4$—$Ni_{1.0}Mo_{0.5}W_{0.5}$—O is the bulk phase with partial substitution of W for Mo. The $NH_4$—NiMo—O catalyst is also representative of known compounds. The catalyst of this invention is illustrated by $NH_4$—$Ni_{1.0}Mo_{0.5}W_{0.5}$—O and the data show the clear advantage of ammonium nickel tungsten molybdate for HDN/HDS activity.

EXAMPLE 10

Preparation of a Bulk Catalyst Composition According to the Solid Route 18.1 kg-ammonium dimolybdate (15.33 kg $MoO_3$) are dissolved in 575 liters water. Subsequently 28.5 kg ammonium metatungstate (24 69 kg $WO_3$) is added to the solution. The resulting solution is preheated up to 90° C. 26.5 kg $NiCO_3$ (49.7% Ni) powder is mixed with water and the resulting paste is added to the ammonium dimolybdate/ammonium metatungstate solution. The resulting mixture is reacted for 7 hours at 89° C.

EXAMPLE 11

Preparation of a Bulk Catalyst Composition According to the Solution Route

In a 1-liter flask, 13.2 g ammonium molybdate (0.075 moles Mo), 18.7 g ammonium metatungstate (0.075 moles W) and 43.6 g nickel nitrate hexahydrate (0.15 moles Ni) were dissolved in 300 ml water so that the resulting pH equaled 4.3. To this solution, a concentrated $NH_4OH$ solution (about 600 ml) was added until the pH reached 10. At this point, some precipitate remained. The solution was refluxed at 100° C. for 3 hours. During this heating, the precipitate dissolved to give a clear blue solution and on further heating, a green precipitate formed. The heating was continued until the pH reached a value between 6.8 and 7.0. The suspension was cooled to room temperature, filtered, washed with water and dried at 120° C. overnight. 18 grams of material were obtained.

EXAMPLE 12

Sample 2110587

657 g of a NiMo—W bulk catalyst composition obtained according to the procedure described in Examples 10 was added to 1362 g of an aqueous slurry containing 125 g of alumina (prepared by precipitation of sodium aluminate and aluminum sulfate). The resulting Ni—Mo—W bulk catalyst—alumina composition was subsequently mixed at 80° C. until an LOI of 31% was obtained. The resulting composition was subsequently extruded and the extrudates were dried at 120° C. for about 90 minutes and subsequently calcined at 385° C. for one hour in air.

EXAMPLE 13

Sample 2110598

The process of Example 10 was repeated except that instead of the alumina suspension, a silica sol containing 10 wt. % silica were applied.

EXAMPLE 14

Sample 2110591

657 g of a Ni—Mo—W bulk catalyst composition obtained according to the procedure described in Example 10 was added to 510 g of a boehmite paste containing 125 g boehmite. The rebuffing paste was mixed at 60° C. to obtain an LOI of 42%. The resulting composition was extruded, dried and calcined as described in Example 12.

EXAMPLE 15

Sample 2110469

The procedure described in Example 10 was repeated except that alumina is present during the preparation of the bulk catalyst composition. To 755 g of the resulting dried Ni—Mo—W bulk catalyst—alumina composition containing 60 g alumina, 461 g water and a small amount of nitric acid were added. The resulting mixture was mixed at 70° C. while evaporating water until an LOI of 34% was obtained. The resulting composition was extruded, dried and calcined as described in Example 12.

EXAMPLE 16

Ammonium molybdate, ammonium tungsten and/or ammonium chromate are dissolved and combined in a first reactor. The temperature is increased to 90° C. The Group VIII salt is dissolved in a second reactor and heated to 90° C. Ammonium hydroxide is added to the first reactor to form a basic solution. The Group VIII metal solution is added to the first dropwise with stirring in 20 minutes. After 30 minutes, the precipitate is filtered and washed. The precipitate is dried overnight at 120° C. and calcined at 385° C.

EXAMPLE 17

The precipitation method of Example 16 was used to prepare a precipitate from ammonium dimolybdate, ammonium meta tungstate and $Fe(III)(NO_3)_3 \cdot 9\,H_2O$ in 98% yield comprising 41.2 wt. % $Fe_2O_3$, 21.3 wt. % $MoO_3$, and 36.9 wt. % $WO_3$. The surface area of the precipitate was 76 m$^2$/g. The pore volume as measured up to 60 nm by BET using the adsorption curve was 0.147 ml/g.

EXAMPLE 18

The precipitation method of Example 16 was used to prepare a precipitate from $Ni(CO_3)_2 \cdot 6H_2O$, $(NH_4)_6Mo_7O_{24} \cdot 4H_2O$, and $(NH_4)_2Cr_2O_7$ in 87.7% yield comprising 52.2 wt. % NiO, 29.4 wt. % $MoO_3$, and 16.6 wt. % $Cr_2O_3$. The surface area of the precipitate was 199 m$^2$/g. The pore volume as measured up to 60 nm by BET using the adsorption curve was 0.276 ml/g.

EXAMPLE 19

The precipitation method of Example 16 was used to prepare a precipitate from $Ni(CO_3)_2 \cdot 6H_2O$, $(NH_4)_6H_2W_{12}O_{40}$, and $(NH_4)_2Cr_2O_7$ in 87.7% yield comprising 44.0 wt. % NiO, 42.4 wt. % $WO_3$, and 11.8 wt. % $Cr_2O_3$. The surface area of the precipitate was 199 m$^2$/g. The pore volume as measured up to 60 nm by BET using the adsorption curve was 0.245 ml/g.

Aromatic Saturation Examples

The ultra high ASAT (aromatics saturation), HDS and HDN activities of the bulk multimetallic catalysts used in the practice of the present invention were demonstrated through co-current hydroprocessing of low sulfur automotive diesel oil (LSADO). Comparison between the activity of the bulk catalysts of the present invention and a conventional commercial supported NiMo on alumina catalyst, commercially available from Criterion under the designation C-411, has been obtained between 650 and 1000 psig. Selected feedstock properties are listed in Table 6. Results are found in Tables 7, 8 and 9.

TABLE 6

Analytical Summary for Low Sulfur Automotive Diesel Oil (LSADO) (FS-9632)

| Test Name | Result(s) |
|---|---|
| Sulfur in Oils | 592 wppm |
| Nitrogen by Antek | 100 wppm |
| Gravity | 35.9 ° API |
| GCD D-2887 | |
| 5.0 wt. % | 420.7° F. (215.9° C.) |
| 50.0 wt. % | 589.6° F. (309.8° C.) |
| 95.0 wt. % | 698.1° F. (370.1° C.) |
| Hydrocarbon Types by SFC | |
| Saturates | 70.69 wt. % |
| Aromatics | 29.31 wt. % |
| 1-Ring Aromatics | 21.16 wt. % |
| 2-Ring Aromatics | 7.23 wt. % |
| 3$^+$-Ring Aromatics | 0.91 wt. % |

EXAMPLE 20

ASAT Activity

In two parallel reactors, 5.0 cc of bulk catalyst of the present invention having a composition $Ni_{1.5}Mo_{0.5}W_{0.5}$ and 5.0 cc of C-411 were charged respectively. After liquid phase sulfiding under the same conditions, the catalysts were used to process a hydrotreated virgin distillate (FS-9632, Table 6). After lineout liquid product of both reactors were analyzed for aromatic contents through SFC (supercritical fluid chromatography method). The results are presented in Table 7.

TABLE 7

Comparison of ASAT Activity between Bulk Cats and C-411 (Example 20)

| Catalyst | Temp (° F.) | Pressure (psig) | SFC Total Aromatics (wt. %) | SFC 2$^+$-Ring Arom. (wt. %) | First Order $k_{ASAT}$ | RVA for ASAT | Gravity (° API) |
|---|---|---|---|---|---|---|---|
| Bulk | 650 | 1000 | 1.83 | 0.11 | 2.77 | 283 | 42.2 |
| C-411 | | | 10.58 | 0.64 | 1.02 | | 39.8 |
| Bulk | 625 | 1000 | 1.46 | 0.07 | 3.24 | 473 | 40.9 |
| C-411 | | | 15.16 | 0.80 | 0.69 | | 38.2 |
| Bulk | 650 | 800 | 5.0* | na | 1.91 | 451 | 40.7 |
| C-411 | | | 19.5* | na | 0.42 | | 38.3 |
| Bulk | 625 | 800 | 5.01 | .24 | 1.91 | 475 | 40.7 |
| C-411 | | | 19.92 | 1.52 | 0.40 | | 38.2 |
| Bulk | 625 | 650 | 10.25 | 0.66 | 1.13 | 433 | 39.6 |
| Co-Bulk (Example 24) | | | | | | | 38.9 |
| C-411 | | | 22.78 | 2.56 | 0.26 | | 37.9 |
| Bulk | 600 | 650 | 14.18 | 0.79 | 0.78 | 698 | 38.8 |
| C-411 | | | 26.30 | 3.70 | 0.11 | | 37.1 |

1.0 LHSV and 2000 SCF/B H$_2$
*estimated from API gravity

EXAMPLE 21

HDS Activity

In two parallel identical reactors were charged respectively 5.0 cc of bulk catalyst of the present invention and 5.0 cc of C-411. After liquid phase sulfiding under the same conditions, the catalysts were used to process a hydrotreated virgin distillate (FS-9632, Table 6). The lineout liquid products of both catalysts were analyzed for sulfur contents by X-ray. The results are presented in Table 7.

EXAMPLE 22

HDS and HDN Activity of Bulk Catalyst

A reactor was charged with 6 cc of bulk catalyst of this invention which was diluted to 8 cc using denstone. After liquid phase sulfiding, the catalyst was used to process a hydrotreated virgin distillate (FS-9632, Table 6). The lineout liquid product was analyzed for sulfur by X-ray and for nitrogen by Antek. Results are presented in Table 8 for sulfur and Table 9 for nitrogen respectively.

EXAMPLE 23

HDS and HDN Activity of C-411, Comparative

A reactor was charged with 6 cc of C-411 which was diluted to 8 cc using denstone. After liquid phase sulfiding, the catalyst was used to process a hydrotreated virgin distillate (FS-9632, Table 6). The lineout liquid product was analyzed for sulfur by X-ray and for nitrogen by Antek. Results are presented respectively in Table 8 for sulfur and in Table 9 for nitrogen.

TABLE 8

Comparison of HDS Activity between Bulk Cats and C-411

| Example | Catalyst | Temp. (° F.) | Pressure (psig) | LHSV | Product Sulfur (wppm) | First Order $k_{HDS}$ | RVA for HDS |
|---|---|---|---|---|---|---|---|
| 22 | Bulk | 600 | 650 | 1 | 15 | 3.7 | 195 |
| 23 | C-411 | | | 1 | 90 | 1.9 | 100 |
| 22 | Bulk | 625 | 650 | 2.3 | 5(2) | 11.0 | 297 |
| 24 | Co-Bulk | | | 2.3 | 30 | 6.8 | 180 |
| 23 | C-411 | | | 2 | 92(4) | 3.7 | 100 |

EXAMPLE 24

ASAT, HDS and HDN Activity of Co Substituted Bulk Cats

Although not limited to Co substituted bulk catalyst modifications, this particular bulk catalyst derivative was tested on the same hydrotreated LSADO (FS-9632). The catalyst of 6 cc was charged in a fixed bed up-flow reactor after dilution to 8 cc using denstone. It was then used in a co-current hydroprocess of the feed after liquid phase sulfiding. The product liquid was analyzed for API (Table 7), sulfur (Table 8) and nitrogen (Table 9).

TABLE 9

Comparison of Hydrodenitrogenation Activity Between Bulk Cats and C-411

| Example | Catalyst | Temp. (° F.) | Pressure (psig) | LHSV | Product Nitrogen (wppm) | First Order $k_{HDN}$ | RVA for HDN' |
|---|---|---|---|---|---|---|---|
| 22 | Bulk | 625 | 650 | 3.8 | 2.5 | 14.0 | 300 |
| 24 | Co-Bulk | 625 | 650 | 3.8 | 6.3 | 10.5 | 228 |
| 23 | C-411 | 625 | 650 | 3.8 | 31 | 4.6 | 100 |

What is claimed is:

1. A multistage hydroprocessing process comprising:

a) reacting a feedstream in a first hydroprocessing stage in the presence of a hydrogen-containing treat gas, the first stage containing one or more reaction zones, each reaction zone operated at first stage hydroprocessing conditions and in the presence of a first hydroprocessing catalyst, thereby resulting in a first liquid product stream;

b) passing the first liquid product stream to a first separation zone where a first vapor phase product stream and a first liquid phase product stream are produced;

c) reacting the first liquid phase product stream of b) above in a second hydrodesprocessing stage in the presence of a hydrogen-containing treat gas, the second hydroprocessing stage containing one or more second stage reaction zones operated at second stage hydroprocessing conditions wherein each reaction zone contains a second hydroprocessing catalyst, thereby resulting in a second liquid product stream having less than about 1,000 wppm sulfur;

d) passing the second liquid product stream of step c) to a second separation zone wherein a second vapor phase stream and a second liquid phase stream are produced;

e) reacting the second liquid phase stream from d) in a third reaction stage in the presence of a hydrogen-containing treat gas, the third hydroprocessing stage containing one or more reaction zones operated at third stage hydroprocessing conditions in the presence of a third hydrotreating catalyst, in order to form a third liquid product stream;

f) passing the third liquid product stream to a third separation zone wherein a third vapor phase stream and a third liquid phase stream are produced; and g) collecting both the third vapor phase stream and the third liquid phase stream;

wherein at least one of the reaction zones of at least one of the hydroprocessing stages contains a bulk multimetallic catalyst comprised of at least one Group VIII non-noble metal and at least two Group VIB metals and wherein the ratio of Group VIB metal to Group VIII non-noble metal is from about 10:1 to about 1:10.

2. The process of claim 1 wherein bulk multimetallic catalyst is present in only the first reaction stage.

3. The process of claim 1 wherein the bulk multimetallic catalyst is present in only the second reaction stage.

4. The process of claim 1 wherein the bulk multimetallic catalyst is present in at least one of:
(i) the first and second reaction stages;
(ii) the first and third reaction stages; and
(iii) the second and third reaction stages.

5. The process of claim 1 wherein the bulk multimetallic catalyst is present only in the third reaction stage.

6. The process of claim 1 wherein the bulk multimetallic catalyst is present in all three reaction stages.

7. The process of claim 1 wherein the Group VIII non-noble metal is selected from Ni and Co and the Group VIB metals are selected from Mo and W.

8. The process of claim 1 wherein the bulk multimetallic is represented by the formula:

$$(X)_b(Mo)_c(W)_dO_z$$

wherein X is one or more a Group VIII non-noble metal, and the molar ratio of b:(c+d) is 0.5/1 to 3/1.

9. The process of claim 8 wherein the molar ratio of b:(c+d) is 0.75/1 to 1.5/1.

10. The process of claim 8 wherein the molar ratio of c:d is preferably >0.01/1.

11. The process of claim 1 wherein the bulk multimetallic catalyst is essentially an amorphous material having a unique X-ray diffraction pattern showing crystalline peaks at d=2.53 Angstroms and d=1.70 Angstroms.

12. The process of claim 1 wherein the feedstock is a hydrocarbon with a boiling point in the range of 25° C. to 575° C., and wherein the first and second stage hydroprocessing conditions include a reaction temperature in the range of about 40° C. to 450° C., a pressure of 5 Bar to 1100 Bar, a space velocity of about 0.3 V/V/Hr to 10 V/V/Hr, and a hydrogen gas treat rate of 100 SCF/B to 1,000 SCF/B.

13. The process of claim 1 wherein the feedstock comprises at least one of naphtha, diesel, heavy gas oil, lube oil, and residuum.

14. The process of claim 13 wherein the feedstock is naphtha boiling in the range of 25° C. to 210° C., and at least one of the first, second, and third stage hydroprocessing conditions include a reaction temperature of 100° C. to 370° C., a pressure of 10 Bar to 60 Bar, a space velocity of 0.5 to 10 V/V/Hr, and a hydrogen gas treat rate of 100 SCF/B to 2,000 SCF/B.

15. The process of claim 13 wherein the feedstock is diesel boiling in the range of 170° C. to 350° C., and at least one of the first, second, and third hydroprocessing conditions include a reaction temperature of 200° C. to 400° C., a pressure of 15 Bar to 110 Bar, a space velocity of 0.5 V/V/Hr to 4 V/V/Hr, and a hydrogen gas treat rate of 500 SCF/B to 6,000 SCF/B.

16. The process of claim 13 wherein the feedstock is heavy gas oil boiling in the range of 325° C. to 475° C., and wherein at least one of the first, second, and third stage hydroprocessing conditions include a reaction temperature of 260° C. to 430° C., a pressure of 15 Bar to 170 Bar, a space velocity of 0.3 V/V/Hr, and a hydrogen gas treat rate of 1,000 SCF/B to 6,000 SCF/B.

17. The process of claim 13 wherein the feedstock is a lubricating oil boiling in the range of 290° C. to 550° C., and wherein at least one of the first, second, and third stage hydroprocessing conditions include a reaction temperature of 200° C. to 450° C., a pressure of 6 Bar to 210 Bar, a space velocity of 0.2 V/V/Hr to 5 V/V/Hr, and a hydrogen gas treat rate of 100 SCF/B to 10,000 SCF/B.

18. The process of claim 9 wherein the feedstock is a residuum having a 10% to 50% boiling range of 575° C., and wherein at least one of the first, second, and third stage hydroprocessing conditions include a reaction temperature of 340° C. to 450° C., a pressure of 65 Bar to 1100 Bar, a space velocity of 0.1 V/V/Hr to 1 V/V/Hr, and a hydrogen gas treat rate of 2,000 SCF/B to 10,000 SCF/B.

19. The process of claim 1 wherein the bulk multimetallic catalyst is in the form of particles having a median diameter of at least 50 nm, a surface area of at least 10 m$^2$/gm, a pore volume ranging from 0.05 to 5 ml/g, and an absence of pores smaller than 1 nm.

20. The process of claim 19 wherein the bulk multimetallic catalyst particle has a core-shell structure.

21. The process of claim 20 wherein at least one of the first, second, and third stage hydroprocessing catalyst further comprises a catalytically effective amount of a second catalyst.

22. The process of claim 21 wherein the second catalyst provides at least one of a desulfurization functionality, a denitrogenation functionality, an aromatics saturation functionality, a cracking functionality, and an isomerization functionality.

23. The process of claim 21 wherein, for the stage(s) containing both the bulk multimetallic catalyst and the second catalyst, the second catalyst is located in at least one of:
(i) a region upstream of the bulk multimetallic catalyst;
(ii) a region containing the bulk multimetallic catalyst; and
(iii) a region downstream of the bulk multimetallic catalyst.

24. A two stage hydroprocessing process comprising:
a) reacting a feedstream in a first hydroprocessing stage in the presence of a hydrogen-containing treat gas, said first hydrotreating stage containing one or more reaction zones, each first stage reaction zone operated at first stage hydroprocessing conditions and in the presence of at least one first stage hydroprocessing catalyst, thereby resulting in a liquid product stream having a sulfur content less than about 3,000 wppm;
b) passing the liquid product stream of the first hydroprocessing stage to a first separation zone where a first vapor phase product stream and a first liquid phase product stream are produced;
c) reacting the first liquid phase product stream of b) in a second hydroprocessing stage in the presence of a hydrogen-containing treat gas, the second hydroprocessing stage containing one or more second stage reaction zones operated at second stage hydroprocessing conditions wherein each second stage reaction zone contains at least one second stage hydroprocessing catalyst;
d) passing the second liquid product stream of step c) to a second separation zone wherein a second vapor phase stream and a second liquid phase stream are produced;
e) collecting both the second vapor phase stream and the second liquid phase stream;
(i) wherein at least one of the first stage and second stage hydroprocessing catalyst comprises a bulk multimetallic catalyst comprised of at least one Group VIII non-noble metal and at least two Group VIB metals and wherein the ratio of Group VIB metals to Group VIII non-noble metal is from about 10:1 to about 1:10;

(ii) wherein the second stage hydroprocessing catalyst in at least one second stage reaction zone is an aromatics saturation catalyst; and
(iii) wherein the second stage hydroprocessing conditions in the second stage reaction zone containing the aromatics saturation catalyst hydrodearomatization conditions include a temperature ranging from about 40° C. to about 400° C., a pressure ranging from about 100 psig to about 3,000 psig, and a liquid hourly space velocity ranging from about 0.3 V/V/Hr to about 2.0 V/V/Hr.

25. The process of claim 24 wherein the aromatics saturation catalyst is the bulk multimetallic catalyst.

26. The process of claim 1 wherein at least one of the first, second, and third stage hydroprocessing catalyst is sulfided.

* * * * *